(12) United States Patent
Edelstam

(10) Patent No.: US 9,849,102 B2
(45) Date of Patent: Dec. 26, 2017

(54) TREATMENT FOR REDUCING INFLAMMATION

(75) Inventor: Greta Edelstam, Saltsjo-Duvnas (SE)

(73) Assignee: ISIFER AB, Kista (SE)

( * ) Notice: Subject to any disclaimer, the term of this patent is extended or adjusted under 35 U.S.C. 154(b) by 916 days.

(21) Appl. No.: 13/698,730

(22) PCT Filed: May 13, 2011

(86) PCT No.: PCT/SE2011/000082
§ 371 (c)(1),
(2), (4) Date: Jan. 25, 2013

(87) PCT Pub. No.: WO2011/145993
PCT Pub. Date: Nov. 24, 2011

(65) Prior Publication Data
US 2013/0116329 A1    May 9, 2013

(30) Foreign Application Priority Data
May 19, 2010   (SE) ...................... 1000533

(51) Int. Cl.
*A01N 37/18*   (2006.01)
*A61K 31/16*   (2006.01)
*A61K 31/167*   (2006.01)

(52) U.S. Cl.
CPC ................................. *A61K 31/167* (2013.01)

(58) Field of Classification Search
USPC ...................................................... 514/626
See application file for complete search history.

(56) References Cited

U.S. PATENT DOCUMENTS 5,977,143 A    11/1999   Edelstam
2008/0182841 A1   7/2008   Levine et al.

FOREIGN PATENT DOCUMENTS

EP    1 158 978    *   6/2005
EP    1158978 B1   10/2005

OTHER PUBLICATIONS

Edelstam et al, The effect of lignocaine on sperm phagocytosis in the pertioneal fluid from women with or without endometriosis, Human Reproduction, 13(5):1353-1356 (1998).
Edelstam et al, A new rapid and effective method for treatment of unexplained infertility, Human Reproduction, 23(4):852-856 (2008).
Tyler, Endometriosis coping with a painful problem, The Female Patient, 21(10 supplement):25-28 (1996).
Doran, The anti-inflammatory effect of local anesthetics, The Pain Clinic, 19(5):207-213 (2007).

* cited by examiner

*Primary Examiner* — Marcos Sznaidman
(74) *Attorney, Agent, or Firm* — Porter Wright Morris & Arthur LLP

(57) ABSTRACT

A method of treating endometriosis in a person by reducing a cytokine MCP-1 related activity level of an endometriosis implant in said person by 50% or more while not affecting a corresponding TNF-α related activity level by more than 30% comprises providing a pharmaceutical composition comprising a local anaesthetic, in particular lidocaine hydrochloride, and a pharmaceutically acceptable carrier, administering the composition intraperitoneally to said person, thereby substantially reducing the recruitment of macrophages by MCP-1 released from the endometriosis implant. Also disclosed is a corresponding pharmaceutical composition.

12 Claims, No Drawings

TREATMENT FOR REDUCING INFLAMMATION

FIELD OF THE INVENTION

The present invention relates to a method of treatment for reducing inflammation, in particular in connection with endometriosis and dysmenorrhea, and to a pharmaceutical composition for use in the method.

BACKGROUND OF THE INVENTION

Altered content of cytokines has been described in peritoneal fluid from patients with endometriosis (1). Cytokines associated to endometriosis, such as TNF-α (tumor necrosis factor), Macrophage Chemotactic Protein-1 (MCP), Interleukin-6 (IL), IL-8 and Chemokine receptor 1 (CCR), are present in the peripheral blood and in the peritoneal fluid (2). There is also an impact on fertility of Interferon-γ (IFN) and Tumor necrosis factor-α (TNF) facilitating ovulation and fertilization whereas IL-1β and colony stimulating factor-1 (CSF) can affect implantation (3). There are also studies on substances such as anti-TNF, which in vitro has been demonstrated to have the capacity of reversing the decreased sperm motility caused by TNF (4). Further there have also been therapeutic approaches to treat endometriosis by regulating the cytokine release such as TNF-binding protein-1 and IL-12 which have proved to be effective in reducing endometriosis lesions (5).

Lidocaine is a well known local anaesthetic of the formula

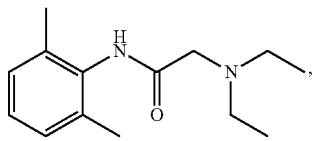 [SMILES: CCN(CC)CC(=O)Nc1c(C)cccc1C]

having membrane stabilizing, anti-arrhythmic and anti-inflammatory properties.

Increased amounts of leukocytes, mainly macrophages, have been found in the peritoneal fluid of women with endometriosis. The exact pathogenesis for endometriosis and the intraperitoneal leukocytosis is unknown. In this study a MCP-1 (Macrophage Chemotactic Protein) production from endometriosis cells has been found. This can contribute to the recruitment of more macrophages in to the peritoneal cavity. The MCP-1 production seems to be reduced by lidocaine. Thereby fewer macrophages might be recruited intraperitoneally and constitute a potential explanation for the clinical effect on pain due to endometriosis and dysmenorrhea. Macrophages are a major source of cytokine production.

OBJECTS OF THE INVENTION

An object of the invention is to provide a method of the aforementioned kind, which provides relief from pain e.g. dysmenorrhea for extended periods of time such as for three months or more, in particular for months or more and even for up to one year or more.

Another object of the invention is to provide a method of the aforementioned kind, which does not affect hormonal levels, in particular estrogen levels, in the patient treated.

Further objects of the invention will become apparent from the following summary of the invention, the description of preferred embodiments thereof, and the appended claims.

SUMMARY OF THE INVENTION

According to the invention is disclosed a method of selectively reducing a cytokine MCP-1 (monocyte chemotactic protein-1) related activity level of an endometriosis implant in a person, providing a pharmaceutical composition comprising lidocaine and a pharmaceutically acceptable carrier; administering an amount of the composition capable of such selective reduction intraperitoneally to said person, thereby substantially suppressing the release of MCP-1 from the endometriosis implants.

In this application, "substantially suppressing" or "substantial suppression" signifies a suppression of a normal level of MCP-1 release by 50% or more, in particular by 70% or more, and even up to 80% or more, while not affecting the release of TNF-1 by more than 30%, in particular by more than 20%, and even by more than 15% or 10%. In the context of the present application a normal level of MCP-1 release is a level in an otherwise healthy individual not under the influence of drugs. "Affecting" is to be understood as affecting positively or negatively.

The method of administration according to the invention is selected from the group consisting of: administration by injection into the peritoneal cavity by means of a syringe, an infusion into the peritoneal cavity by means of a catheter, a preoperative deposition in the abdominal cavity, a transdermal absorption via the abdominal wall or a subcutaneous deposition. For transdermal absorption lidocaine patches known in the art applied to the abdoment of the patient. Sustained or delayed release preparations comprising lidocaine known in the art can be deposited preoperatively in the abdominal cavity or injected, such as in form of microbeads comprising lidocaine, or can be deposited subcutaneously in the abdomen.

A preferred concentration of aqueous lidocaine hydrochloride, preferably in form of a balanced salt solution, administered according to the method of the invention is from 0.1 mg/ml to 2.5 mg/ml, more preferred from 0.3 mg/ml to 1.5 mg per ml, most preferred about 1.0 mg/ml in a volume of from 5 ml to 20 ml, in particular of about 10 ml of the solution.

An example of a preferred balanced salt solution is Ringer's solution. For transdermal absorption of lidocaine via the abdominal wall carriers corresponding to those of lidocaine compositions for local dermal anesthesia, such as Emla®, can be used. Lidocaine is preferably administered in form of its hydrochloride. In this application, the term "lidocaine" comprises pharmaceutically acceptable salts thereof, such as the hydrochloride.

According to a preferred aspect of the invention, the method of the invention is capable of substantially reducing the recruitment of macrophages to the abdominal cavity in a person.

More generally, the method of the invention is useful in reducing the recruitment of macrophages in inflammatory conditions other than endometriosis.

The invention will now described in greater detail by reference to a number of of preferred examples thereof.

DETAILED DESCRIPTION OF THE INVENTION

Preparing Cultures of Endometriosis Cells.

During laparotomy, human endometriosis tissue biopsies from endometriosis cysts were obtained from four women during laparotomy. The tissue samples were handled aseptically, transported to the laboratory and frozen in fluid nitrogen to −150° C. The biopsies were later verified histologically as endometriosis tissue. The sampling procedure was approved by the Ethical Committee. The frozen endometriosis tissues were thawed in water at +37° C. and then transferred to test tubes. Two tissue biopsy samples were taken from each endometrioma and prepared as follows: the endometriosis tissue covering the inside of endometriosis cysts was detached from encapsulating fibrous tissue by gentle scraping with a knife. The tissue was then exposed for 0.2% collagenase Type III (Worthington Biochemical Corporation Freehold, N.J., USA) for 2 h. The cell suspension was then centrifuged at 1500 rpm for 10 min. The cells were re-suspended in RPMI 1640 cell culture medium with L-glutamine and phenol red (Invitrogen Ltd), 20% Foetal Bovine serum (Invitrogen Ltd), sodium pyruvate, MEM 100 mM (Invitrogen Ltd), non-essential amino acids (Invitrogen Ltd), heparin 90 μg/ml (Sigma-Aldrich Fine Chemicals St Louis, Mo., USA), penicillin-streptomycin with 10.000 Units/ml penicillin G sodium and 10.000 μg/ml streptomycin sulphate in 0.85% saline (Invitrogen Ltd), Hepes buffer solution 1M (Invitrogen Ltd) and seeded in T-75 cm² cell culture flasks (Nunc, Roskilde, Denmark) pre-coated with 0.2% gelatin (Sigma-Aldrich). The culture medium was changed the following day and thereafter once a week. When confluent monolayers were obtained after 3 weeks, the cultures were tryptinized cultures from passages 4 and 6 were frozen in fluid nitrogen to −150° C. and later used for experiments.

Incubations of Endometriosis Cells and Lidocaine.

The lidocaine treatments of the cells were performed in duplicates on the endometriosis cells that were used for experiments. The thawed cells were re-suspended in RPMI 1640 cell culture medium with L-glutamine and phenol red (21875-042 Invitrogen, Stockholm, Sweden Invitrogen Ltd) including 15% Foetal Bovine serum (cat. nr. 10270-106 Invitrogen, Stockholm, Sweden Invitrogen Ltd), 0.8% sodium pyruvate, 1% Hepes (cat. nr. 15630-056, Invitrogen, Stockholm, Sweden), 0.8% ECGS (cat. no. 354006, Becton-Dickinson), 0.8% MEM non-essential amino acids (cat. no. 11140-035 Invitrogen, Stockholm, Sweden Invitrogen Ltd), Heparin 90 μg/ml (cat. no. H3149 Sigma-Aldrich Fine Chemicals St. Louis, Mo., USA), penicillin-streptomycin with 10.000 Units/ml penicillin G sodium and 10.000 μg/ml streptomycin sulphate in 0.85% saline (cat. no. 151140-122, Invitrogen, Stockholm, Sweden), and seeded in T-25 cm 2 cell culture flasks (Nunc, Roskilde, Denmark) pre-coated with 0.2% gelatin (Sigma-Aldrich) and maintained in a 5% $CO_2$/95% humidified air atmosphere at 37° C. The cells were incubated with added lidocaine hydrochloride at a final concentration of 1 mg/ml. The lidocaine treatment had duration of 24 and 48 hours respectively. In the control cultures there was no addition of lidocaine to the incubation medium. After incubation the culture media was collected and snap frozen −70° C. The production of MCP-1, TNF-α and IL-6β was measured according to the manufacturer's using an enzyme-linked immunosorbent assay (ELISA, Quantikine, R&D Systems, Minneapolis, Minn. 55413, USA).

In Vitro Results.

The ELISA analyses showed a reduced cytokine production from the endometriosis cells during incubation with lidocaine. A substantial reduction of MCP-1 was noted whereas the production of TNF-α was unaffected. The concentration of IL-1β in the cell medium was at a low level both before and after incubation with lidocaine (Table 1).

TABLE 1

| Cytokine, pg/ml | Control medium endometrium | Control medium 24 h | Lidocaine medium 24 h | Control medium 48 h | Lidocaine medium 48 h |
| --- | --- | --- | --- | --- | --- |
| MCP-1 | <31.25 | 145.0 | 62.0 | 315.0 | 122.0 |
| TNF-α | 7.3 | 8.2 | 9.4 | 10.5 | 10.0 |
| IL-1β | <5.00 | <5.00 | <5.00 | <5.00 | <5.00 |

Treatment of Endometriosis by Selectively Reducing Release of MCP-1 by Endometric Cells while not Substantially Effecting the Release of TNF-α from the Same Cells.

To a female subject diagnosed with inflammation caused by endometriosis is administered intraperitoneally a single dose of 10 ml of saline comprising 1 mg/ml of lidocaine. hydrochloride.

REFERENCES

1. Hao M, Shi Y, Dong M. *Measurements of interleukin-6, interleukin-8 and transforming growth factor-beta 1 levels in peritoneal fluid of patients with endometriosis.* Zhonghua Fu Chan Ke Za Zhi. 2000; 35 (6):329-31.
2. Agic A, Xu H, Finas D, Banz C, Diedrich K, Hornung D. *Is endometriosis associated with systemic subclinical inflammation?* Gynecol Obstet Invest. 2006; 62 (3):139-47.
3. Vassiliadis S, Relakis K, Papageorgiou A, Athanassakis I. *Endometriosis and infertility: a multi-cytokine imbalance versus ovulation, fertilization and early embryo development.* Clin Dev Immunol. 2005 June; 12 (2):125-9.
4. Eisermann J, Register K B, Strickler R C, Collins J L. *The effect of tumor necrosis factor on human sperm motility in vitro.* J Androl. 1989 July-August; 10 (4):270-4.
5. Fedele L, Berlanda N. *Emerging drugs for endometriosis.* Expert Opin Emerg Drugs. 2004 May; 9 (1):167-77.
6. Edelstam G A B, Lundkvist EÖ, Fraser B, Laurent U B G, Laurent T C. *The concentration and turnover of intraperitoneal hyaluronan during inflammation.* Inflammation. 1992; 16 (5): 459-469.
7. Halis G, Arici A. *Endometriosis and inflammation in infertility.* Ann N Y Acad Sci 2004; 1034, 300-15.
8. Sidell N, Han S W, Parthasarathy S. *Regulation and modulation of abnormal immune responses in endometriosis.* Ann N Y Acad Sci. 2002; 955:159-73.

The invention claimed is:

1. A method of treating endometriosis in a person suffering from inflammation due to endometriosis and having an endometriosis implant, by reducing a cytokine MCP-1 related activity level of the endometriosis implant in said person by 70% or more while not affecting a corresponding TNF-α related activity level by more than 20%, comprising intraperitoneally administering a pharmaceutical composition comprising lidocaine hydrochloride and a pharmaceutically acceptable aqueous balanced salt solution to said person, wherein the pharmaceutical composition is administered by injection or infusion into the peritoneal cavity and wherein the pharmaceutical composition comprises from 0.8 mg/ml to 2.5 mg/ml of lidocaine hydrochloride and is administered into the peritoneal cavity in an amount of from 5 ml to 20 ml.

2. The method of claim 1, wherein the pharmaceutical composition comprises about 1.0 mg/ml of lidocaine hydrochloride and is administered into the peritoneal cavity in an amount of from 5 ml to 20 ml.

3. The method of claim 1, wherein pharmaceutical composition comprises about 1.0 mg/ml of lidocaine hydrochloride and is administered into the peritoneal cavity in an amount of about 10 ml.

4. The method of claim 1, wherein administration is by injection into the peritoneal cavity by means of a syringe.

5. The method of claim 1, wherein administration is by infusion into the peritoneal cavity by means of a catheter.

6. The method of claim 1, wherein the pharmaceutically acceptable aqueous balanced salt solution is Ringer's solution.

7. A method of treating endometriosis in a person suffering from inflammation due to endometriosis and having an endometriosis implant, comprising intraperitoneally administering a pharmaceutical composition comprising lidocaine hydrochloride and Ringer's solution to said person, wherein the pharmaceutical composition is administered by injection or infusion into the peritoneal cavity and wherein the pharmaceutical composition comprises about 1.0 mg/ml of lidocaine hydrochloride and is administered into the peritoneal cavity in an amount of from 5 ml to 20 ml.

8. The method of claim 7, wherein the amount of lidocaine hydrochloride administered into the peritoneal cavity is about 1.0 mg/ml in a volume of about 10 ml of an aqueous carrier.

9. The method of claim 7, wherein administration is by injection into the peritoneal cavity by means of a syringe.

10. The method of claim 7, wherein administration is by infusion into the peritoneal cavity by means of a catheter.

11. A method of treating endometriosis in a person suffering from inflammation due to endometriosis and having an endometriosis implant, comprising intraperitoneally administering a pharmaceutical composition comprising lidocaine hydrochloride and a pharmaceutically acceptable aqueous balanced salt solution to said person, wherein the pharmaceutical composition is administered by injection with a syringe or by infusion with a catheter into the peritoneal cavity and wherein the pharmaceutical composition comprises about 1.0 mg/ml of lidocaine hydrochloride and is administered into the peritoneal cavity in an amount of 10 ml.

12. The method of claim 11, wherein the pharmaceutically acceptable aqueous balanced salt solution is Ringer's solution.

* * * * *